United States Patent [19]
Ron

[11] Patent Number: 5,876,741
[45] Date of Patent: Mar. 2, 1999

[54] CHEMO-MECHANICAL EXPANSION DELIVERY SYSTEM

[75] Inventor: Eyal S. Ron, Lexington, Mass.

[73] Assignee: MedLogic Global Corporation, Colorado Springs, Colo.

[21] Appl. No.: 892,920

[22] Filed: Jul. 15, 1997

Related U.S. Application Data

[63] Continuation-in-part of Ser. No. 749,758, Oct. 22, 1996, which is a continuation-in-part of Ser. No. 473,218, Jun. 7, 1995, Pat. No. 5,651,979, which is a continuation-in-part of Ser. No. 413,409, Mar. 30, 1995.

[60] Provisional application No. 60/022,092 Jul. 16, 1996.

[51] Int. Cl.$^6$ .................................. A61F 2/02; A61K 9/22
[52] U.S. Cl. .................... 424/423; 604/891.1; 604/892.1
[58] Field of Search .................... 424/423; 604/892.1, 604/891.1

[56] References Cited

U.S. PATENT DOCUMENTS

| | | |
|---|---|---|
| 4,034,756 | 7/1977 | Higuchi et al. . |
| 4,180,073 | 12/1979 | Michaels . |
| 4,235,236 | 11/1980 | Theeuwes . |
| 4,327,725 | 5/1982 | Cortese et al. .................... 128/260 |

FOREIGN PATENT DOCUMENTS

| | | |
|---|---|---|
| WO92 05775 | 4/1992 | WIPO . |
| WO96 02276 | 2/1996 | WIPO . |
| WO96 40082 | 12/1996 | WIPO . |

*Primary Examiner*—Carlos A. Azpuru
*Attorney, Agent, or Firm*—Burns, Doane, Swecker & Mathis, L.L.P.

[57] ABSTRACT

System for delivery of a biologically active substance into an environment. The container is comprised of a single member or two mated members and defines first and second compartments. The container includes pores in at least a portion of the container defining the first compartment. The first compartment contains a polymer gel network which undergoes a volume expansion in response to an environmental condition which varies in the biological environment. The second compartment contains an effective amount of a biologically active compound and may include at least one passageway communicating with the biological environment. Drug delivery is initiated and continues only when the appropriate environmental condition or trigger is met, whereupon volume expansion of the polymer gel network causes the biologically active compound to be discharged into the biological environment.

21 Claims, 8 Drawing Sheets

CHEMO-MECHANICAL EXPANSION DELIVERY SYSTEM

This application is a continuation-in-part application of co-pending application U.S. Ser. No. 08/749,758 filed Oct. 22, 1996, which is a continuation-in-part application of application U.S. Ser. No. 08/473,218, filed Jun. 7, 1995 now U.S. Pat. No. 5,651,979, which is a continuation-in-part application U.S. Ser. No. 08/413,409, filed Mar. 30, 1995, the entire contents of which are incorporated herein by reference.

This application also claims priority under 35 U.S.C. §119(e) from U.S. Provisional Application No. 60/022,092, filed Jul. 16, 1996, the entire contents of which are incorporated herein by reference.

BACKGROUND OF THE INVENTION

This invention relates to method and apparatus for delivering a biologically active compound to a biological environment in a controlled fashion.

The more precise control of the release of orally administered drugs has long been sought. In particular, it is desired that an orally administered drug or other biologically active compound be released only upon the occurrence of a desired environmental condition within a biological system. For example, it may be desired that a biologically active compound be released only in the intestines rather than being released as the material passes through the mouth and stomach. Prior art controlled release techniques typically result in initiation and/or continuation of controlled release as a function of time after ingestion.

An example of a controlled release oral delivery system is the so-called osmotically-controlled delivery system. See, for example, Wang et al., U.S. Pat. No. 5,413,572; Theeuwes et al., U.S. Pat. No. 3,845,770; Wang, U.S. Pat. No. 5,312,390; Eckenhoff et al., U.S. Pat. No. 4,474,575; Place et al., U.S. Pat. No. 5,147,654; Eckenhoff et al., U.S. Pat. No. 4,539,004; Magruder et al., U.S. Pat. No. 4,777,049; and EP 0 427 519 A2. The technology disclosed in these patents utilizes the osmotic pressure resulting from concentration gradients to expel a biologically active substance into the body. In some embodiments, the osmotic pressure moves a moveable partition to effect drug release. Wang et al., in the '572 patent, also teaches the use of a hydrogel which expands when contacted with water, the expansion serving to expel the biologically active material.

Osmotic pressure based systems have the shortcoming that they depend on flux and pressure for their operation. It is known that a desirable drug delivery system should be independent of both flux and pressure. In addition, an osmotic pressure based system has release kinetics that are highly dependent on orifice size. The osmotic pumps of the prior art operate on the principle of net flux of water across a semipermeable membrane into a compartment that contains the osmotic driving agent. The rate of flux is controlled by the water permeable membrane characteristics and the difference in osmotic and hydrostatic pressure between the compartment containing the osmotic driving agent and the outside of the device. The flux J of water may be represented as $J=K \cdot A \cdot (\sigma \cdot \Delta\pi - \Delta P)$ where K is the permeability of the membrane, A is the membrane's surface area, $\sigma$ is the osmotic coefficient of the membrane, $\Delta\pi$ is the osmotic pressure and $\Delta P$ is the hydrostatic pressure. See, Theeuwes et al., "Principles of the Design and Operation of Generic Osmotic Pumps for the Delivery of Semisolid or Liquid Drug Formulations," *Annals of Biomed. Eng.*, 4(343), 1976.

As stated above, the prior art osmotic systems are also very sensitive to the size of the delivery orifice. See, Theeuwes et al., "Elementary Osmotic Pump," *J. Pharm. Sci.*, 64(1987), 1975. The orifice size must be small so as to minimize diffusion through the orifice and yet still be sufficiently large to minimize hydrostatic pressure inside the system that would affect the zero-order release kinetics. Further, the release kinetics in osmotic systems are independent of pH and motility of the gastrointestinal tract. See, Fara et al., "Osmotic Pumps in Drug Delivery Devices—Fundamentals and Applications," Praveen Tyle, ed., Marcel Dekker, Inc., p137 (New York).

Other systems for non-continuous delivery of drugs, for example, the Pulsncap system are known in the prior art. In this system there is a limiting osmotic pressure which, when achieved, pushes out a cap to begin drug release.

Reference is also made to the prior art connection of an osmotic system to a syringe-like system to provide an external continuous IV/IM/SQ infusion. See, U.S. Pat. No. 3,604,417 and Urquhart et al., "Rate-Controlled Delivery Systems in Drug and Hormone Research," *Ann. Rev. Pharmacol. Toxicol.*, 24(199), 1984.

In none of the prior art delivery systems is there initiation and continuation of release upon the occurrence of an environmental condition such as pH which changes from place to place within the body.

Volumetric change phenomena have been observed in three-dimensional, permanently crosslinked polymer gel networks. As an external environmental condition (e.g., temperature, solvent composition, pH, electric field, light intensity and wavelength, pressure, ionic strength, osmolarity) is changed, the polymer gel network contracts and/or expands in volume. The volume of such a gel may, under certain circumstances, change reversibly by a factor as large as several hundred when the gel is presented with a particular external condition (i.e., the gel is a "responsive" gel; see, for example, Tanaka *Phys. Rev. Lett.* 40(820), 1978; Tanaka et al., *Phys. Rev. Lett.* 38(771), 1977; Tanaka et al., *Phys. Rev. Lett.* 45(1636), 1980; Ilavsky, *Macromolec.* 15(782), 1982; Hrouz et al., *Europ. Polym. J.* 17, p361, 1981; Ohmine et al., *J. Chem. Phys.* 8(6379), 1984; Tanaka et al., *Science* 218(462), 1982; Ilavsky et al., *Polymer Bull.* 7(107), 1982; Gehrke "Responsive Gels: Volume Transitions II", Dusek (ed.), Springer-Verlag, New York, p81–144, 1993; Li et al., *Ann. Rev. Mat. Sci.* 22(243), 1992; and Galaev et al., *Enzyme Microb. Technol.* 15(354), 1993, each of which is incorporated herein by reference).

Interpenetrating network polymers have also demonstrated similar volume change phenomena; see, for example, Tanaka et al. in U.S. Pat. No. 5,403,893 and Tanaka et al. in U.S. Pat. No. 5,580,929.

Thermally responsive polymers have been used in the preparation of delivery devices in which release of a biologically active agent into the host is dependent upon the temperature; see, R. Dinarvand and A. D'Emanuele, *J. Control. Res.* 36(3): 221 (October 1995). The devise incorporates the thermally responsive polymer as a valve which is swollen (and closed) at room temperature and contracted (an open) at biological temperatures. Thus, the polymer functions as an on-off switch, but has no means of actively delivering the active agent into the environment.

In a similar fashion, Bae et al (U.S. Pat. No. 5,226,902) report a drug delivery device which includes a hydrogel swollen with a solution containing a biologically active agent. The hydrogel is capable of contracting under certain environmental conditions. As the hydrogel contracts, the agent is released into the portion of the device previously occupied by the swollen hydrogel. The device provides orifices which allow movement of the agent out of the device; however, there is no means of active delivery of the active agent into the environment.

The desire to release drugs/agents into physiological fluids is well recognized. The ability to obtain linear or other desired pharmocodynamics to eliminate the peaks and troughs associated with other oral delivery formulations is a goal commonly accepted as difficult to obtain.

SUMMARY OF THE INVENTION

It is the object of the invention to provide a drug delivery system in which the kinetics of swelling of the expanding polymer hydrogel can be controlled; hence thereby controlling the kinetics of delivery of the active component.

It is a further object of the invention that a drug delivery device be provided which provides improved control over the mode of delivery of the bioactive and over the kinetics of the deliver.

It is also desired to improve the engineering design of the device to achieve these and other objects of the invention.

In one aspect of the invention an apparatus for controlled delivery of a biologically active compound to a biological environment is provided which includes a container comprised of a single member or two mated members, the container defining first and second compartments and comprising pores in at least a portion of the container defining the first compartment. The first compartment contains a polymer gel network which undergoes a volume expansion in response to an environmental condition which varies in the biological environment. The second compartment contains an effective amount of a biologically active compound and including at least one passageway communicating with the biological environment. Upon volume expansion of the polymer gel network, the biologically active compound is discharged into the biological environment through the passageway.

By "pores" as that term is used herein it is meant a passageway in a material through which fluid can pass with no control of flow direction or rate. "Pores" may encompass passageways of any size, including conventional "screens" of large dimension and ranging down to "membranes" of small dimension.

In another aspect of the invention, an apparatus for controlled delivery of a biologically active compound to a biological environment includes a container comprising pores in at least a portion of the container. A first compartment within the container contains a polymer gel network which undergoes a volume expansion in response to an environmental condition which varies in the biological environment. A second compartment contains an effective amount of a biologically active compound and including at least one passageway communicating with the biological environment. The second compartment is disposed within the first compartment.

In another aspect of the invention, an apparatus for controlled delivery of a biologically active compound to a biological environment includes a container comprising pores in at least a portion of the container. A first compartment within the container contains a polymer gel network which undergoes a volume expansion in response to an environmental condition which varies in the biological environment. A second compartment contains an effective amount of a biologically active compound in communication with the biological environment through the pores, the first compartment disposed within the second compartment.

In yet another aspect of the invention, an apparatus for controlled delivery of a biologically active compound to a biological environment includes a container comprised of a single member or two mated and comprising pores in at least a portion of the container, the container defining a space housing upper and lower compartments containing a polymer gel network which undergoes a volume expansion in response to an environmental condition which varies in the biological environment. The upper and lower compartment are in communication with the biological environment through the container pores. An inner compartment contains an effective amount of a biologically active compound and including at least one passageway communicating with the biological environment.

In the above devices, drug delivery is initiated and continues only when the appropriate environmental condition or trigger is met, whereupon volume expansion of the polymer gel network causes the biologically active compound to be discharged into the biological environment through the passageway.

DESCRIPTION OF THE PREFERRED EMBODIMENT

In its most general principle, the chemo-mechanical delivery system of the present invention consists of a biologically active component, e.g., a drug, to be delivered, and an environmentally responsive, volume expandable hydrogel enclosed within a container which permits communication of the interior with its environment. By "environmentally responsive, volume expandable hydrogel" as that term is used herein, it is meant a hydrogel which experiences an increase in volume upon exposure to a predetermined environmental condition. The chemo-mechanical delivery system may be designed to provide time-based release of the biologically active component. It can also be designed to provide linear, non-linear or pulsatile drug delivery, as desired, over a specific time period in the presence of pre-determined trigger, such as pH. Taken orally, as the device moves through the digestive tract, the hydrogel can be designed to swell in response to changes in the environment, such as pH, releasing the pharmaceutic at a controlled rate that can range from a few minutes to over 24 hours.

A major advantage of the chemo-mechanical drug delivery system is that delivery is not dependent upon residence time in the digestive tract. Many conventional timed-release designs are limited because they depend on an estimate of residence time of the drug capsule as it moves through the digestive system. Because the residence/transport time in humans from time of uptake is variable, this presents a serious challenge to effective drug delivery.

An addition advantage is that the release rates from the chemo-mechanical drug delivery system can be designed to be independent of the drug's properties. The system could also logically contain different hydrogels that will provide swelling kinetics in response to different stimuli or different levels of the same stimuli (e.g., different pH levels) and thereby provide a nonlinear or pulsatile release.

The device and method of its use described herein provide a superior delivery system because it allows for the initiation of drug release at a desired pH, release rates that are independent of drug properties and delivery of compounds of heretofore difficult to deliver bioactive components, e.g., macromolecules, unusual ionic species, labile, lyophilic, insoluble and other drugs that require unique formulations.

Figure 1:
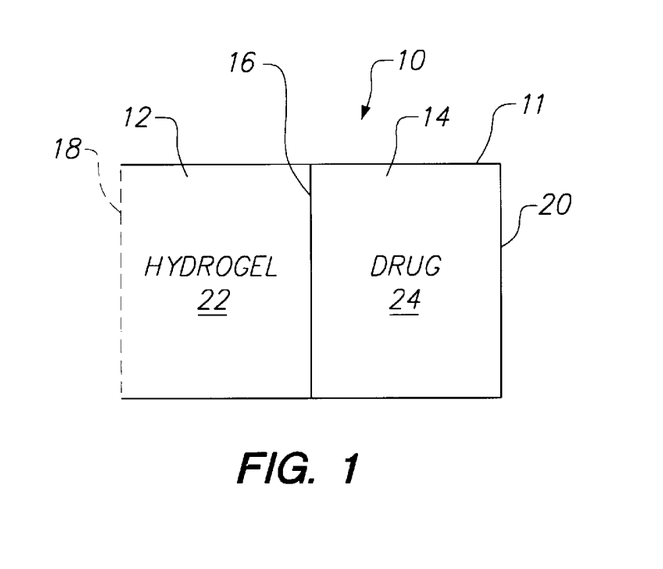
FIG. 1 is a cross-sectional view of an embodiment of the invention disclosed herein.

With reference to FIG. 1, a drug delivery system 10 includes a container 11 encompassing a first compartment or region 12 and a second compartment or region 14. The regions 12 and 14 may be adjacent to one another or they may be separated by an optional partition 16. The container 11 includes pores 18 which may occupy a small portion of the container surface area (in proximity to the region 12) or which may occupy substantially the entire surface area of the container 11. The second compartment 14 may include at least one passageway 20. First compartment 12 contains environmentally responsive, volume expandable hydrogel 22 and the second compartment 14 contains a biologically active material or drug 24. The pores 18 retain the hydrogel 22 within the compartment 12 but allow communication with fluids in a biological environment (not shown) into which the device 10 is placed. The pores 18 may form a permeable or semipermeable membrane as desired.

As has been discussed previously, the hydrogel 22 is selected to undergo a volume expansion in response to the occurrence of an environmental condition such as pH. Upon occurrence of such a condition, the hydrogel 22 will expand, thereby displacing the compartment or region of the hydrogel to the right in FIG. 1. This movement will decrease the volume in the second compartment 14, causing the biologically active material 24 to exit through the passageway 20 into a biological environment (not shown). Alternatively, in embodiments where the device instead includes pores 18 over the entire container surface, the pores may serve as the passageway and the biologically active material 24 may exit through pores 18 in the container defining the second compartment.

In use, the device 10 would be placed into the mouth and swallowed. The pH of the esophagus and stomach are low so that no drug is released. When, however, the device 10 reaches the intestines, there will be encountered an environment having a higher pH. Communication with the higher pH environment through the pores 18 causes the hydrogel 22 to expand to expel the drug 24 into the intestinal region. It will be recognized and appreciated that following the teachings of this application and applications Ser. Nos. WO 96/02276 published Feb. 1, 1996, 08/473,218 and 08/749,758, which are incorporated herein by reference their entirety, permit the design and engineering of hydrogels which undergo a volume expansion at a desired environmental condition or in a range of environmental conditions. In another embodiment, the gel in the device 10 may be triggered by a gradient in an ionic species in solution, for example, a potassium ion gradient. Such a trigger has application to drug delivery into the gastrointestinal tract.

Figure 2:
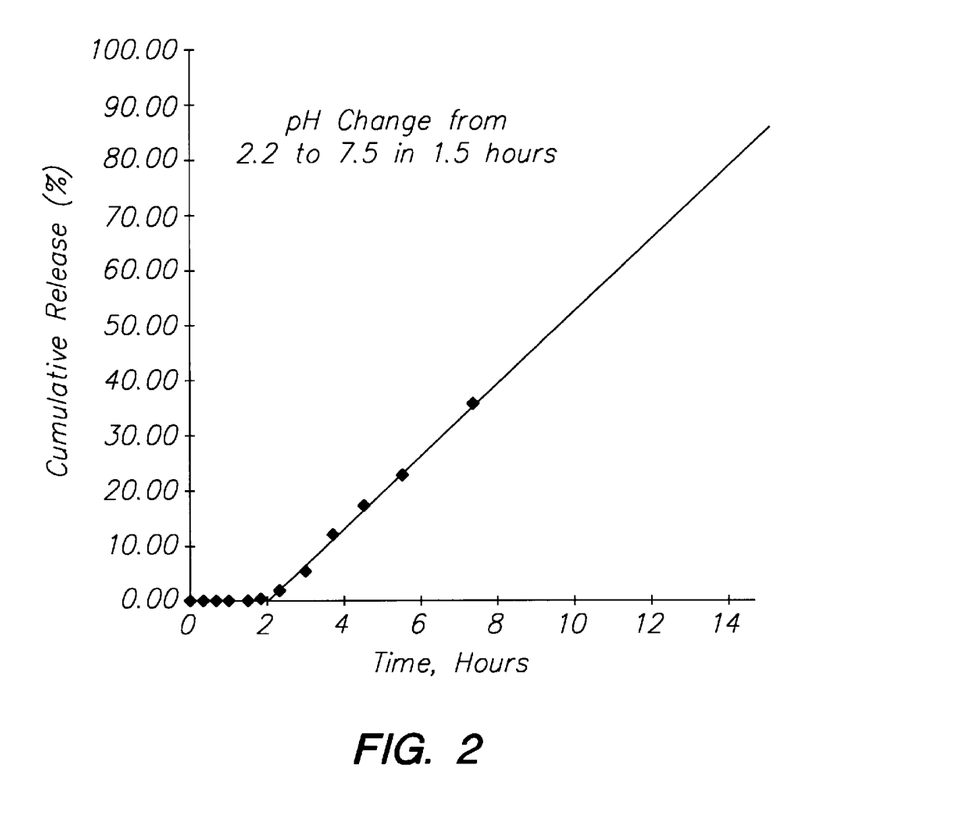
FIG. 2 is a graph of cumulative release versus time.

With reference to FIG. 2, there is shown the cumulative release of a viscous hydrophilic material (0.5% Carbopol 934P, neutralized) measured at pH 2.2 (glycine buffer) for 1.5 hours, representing gastric residence time. The apparatus was then placed in a vessel containing Simulated Intestinal Fluid, USP (pH 7.5). This graph shows that there was no release of the material at low pH followed by release after the pH was raised to 7.5. In the experiment whose response is illustrated in FIG. 2, the hydrogel was hydroxypropylcellulose crosslinked with adipic acid. A gel having the response characteristics illustrated in FIG. 2 is suitable for a controlled release of a drug into the intestines.

Figure 3:
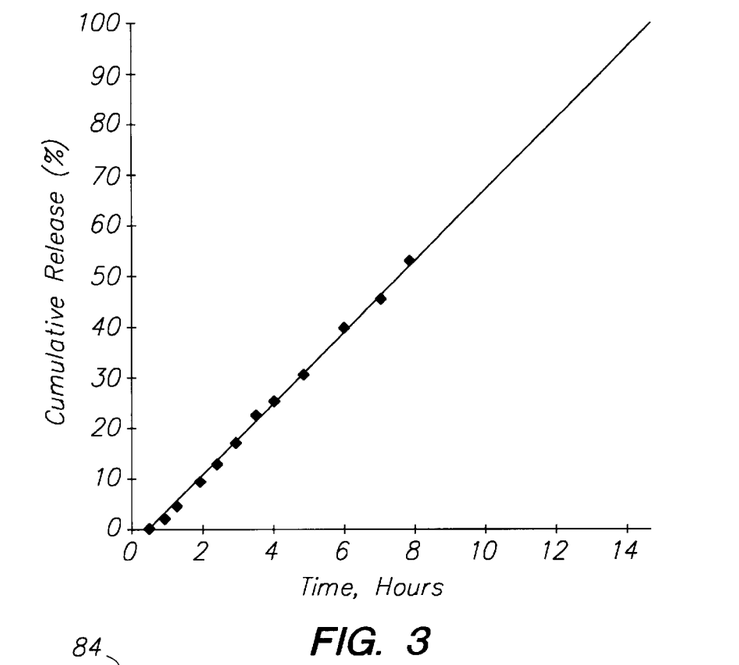
FIG. 3 is a graph of cumulative release versus time of a hydrophobic material into an aqueous environment.

FIG. 3 illustrates the result of an experiment in which a hydrophobic material was released into an aqueous environment. A hydrophobic material, a mixture petrolatum and mineral oil, was placed into the experimental apparatus simulating the device in FIG. 1. The loaded system was then placed into a beaker containing a buffer. Cumulative release was measured by weighing the amount of petrolatum/mineral oil emitted from the apparatus and plotting the percent released over time. The hydrogel used to generate the expansion force was hydroxypropylcellulose crosslinked lightly with adipoyl chloride. This experiment demonstrates zero-order release of a hydrophobic material into a hydrophilic environment to complement the delivery of a hydrophilic material (FIG. 2), thereby indicating the ability of the apparatus of the present invention to deliver formulations irrespective of their physicochemical properties.

These experiments demonstrate that it is possible to release a component into its environment upon introduction of a triggering environmental change. It is desired to develop a device which may be structured and arranged so as to permit any desired release kinetics. For example, it may be desirable in some circumstances to have a linear release of the bioactive material. In other circumstances, it may be desirable to have rapid non-linear release occurring at a pre-determined point in the digestive tract. The advantage of the chemo-mechanical delivery system of the invention is its ability to allow design and engineering of the release kinetics based on manipulation of the environmentally responsive, volume expandable hydrogel and the ability to precisely control its swell kinetics.

The device further may be designed to take advantage of an important difference from existing technology which is dependent on osmotic forces. Osmotic fluid uptake is sensitive to applied pressure. Osmotic forces require semipermeable membranes which allow one-way flow of liquid into the device. In contrast, the chemo-mechanical system requires simply a permeable membrane or screen which is capable of fluid flow in both directions. Because the hydrogel will only expand (swell) in the proper triggering environment, there is no need use a semi-permeable membrane.

Figure 4:
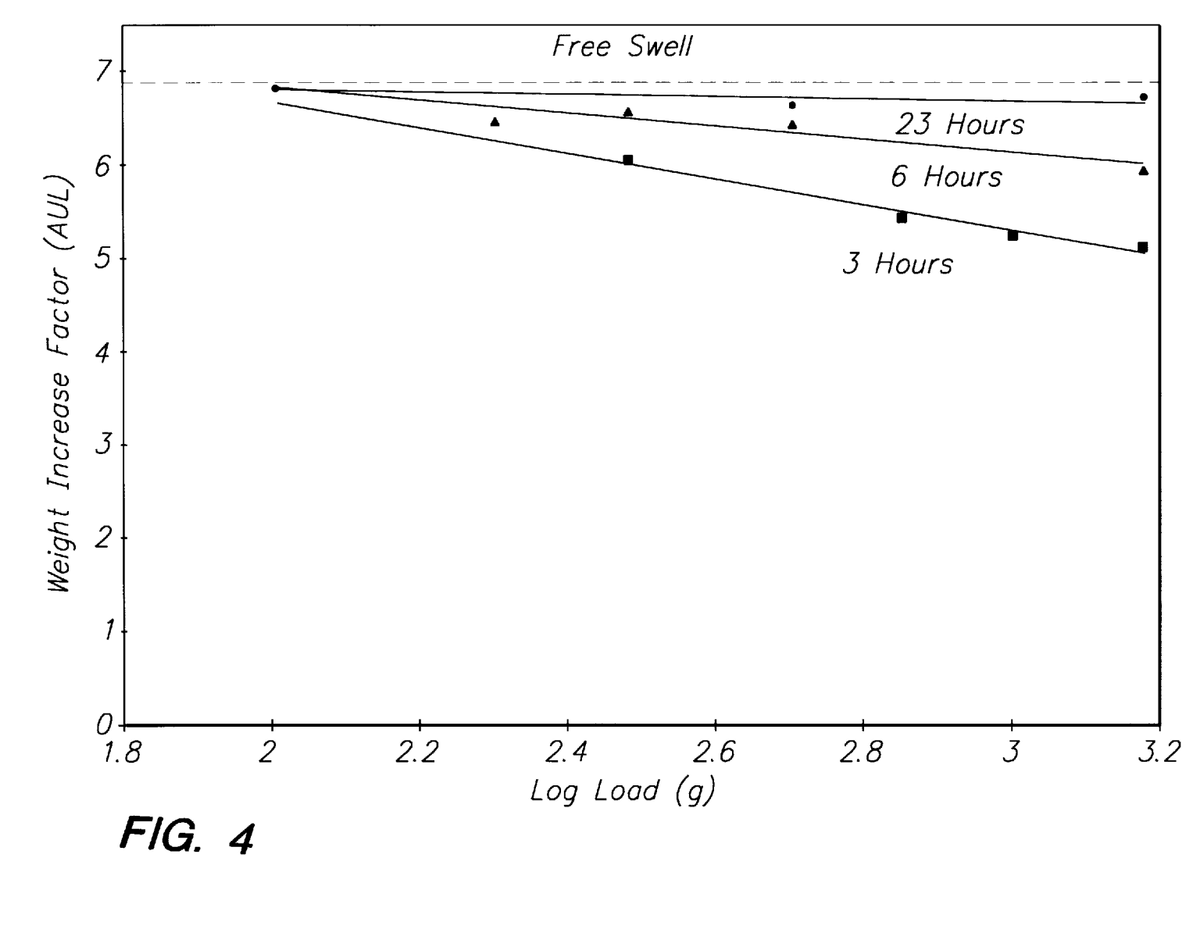
FIG. 4 is a graph of hydrogel weight increase factor versus hydrostatic pressure (log load)

The hydrogel 22 in the compartment 12 is substantially independent of hydrostatic pressure as shown in the curves in FIG. 4. The material used in FIG. 4 is hydroxypropylcellulose (HPC) crosslinked with adipic acid. Volume expansion of the hydrogel against a load (to simulate hydrostatic pressure) was determined over time. Regardless of the magnitude of hydrostatic pressure on the hydrogel, the gel achieved its free swelling volume (expansion in the absence of a load) within about 24 hours. This confirms that the pore design is not a critical factor for the successful fluid uptake in a drug delivery device of the invention.

In a simple two compartment device, the hydrogel and the biologically active agent are located in two separate compartments or regions of a container structure. The container may be comprised of a single member defining the two compartments. Alternatively, the container may be comprised of discreet members defining the hydrogel and biologically active agent compartments, respectively, which are mated to form the container. The two members comprising the container may be joined by methods known in the art such as crimping.

The container may be made from inert non-erodible materials such as thermoplastic polymers (e.g., polyethylene, polyfluoroethylene, polyurethane, etc.), ethylene vinylacetate, polyvinylidene difluoride, polycarbonate, polyhydroxyethyl methacrylate, polyvinylpirrolidone, polyacrylamide, polystyrene, cellulosic derivatives (e.g., cellulose esters, cellulose ethers, cellulose acrylate, cellulose acetate, cellulose butyrate, cellulose propionate, ethylcellulose, hydroxypropyl methylcellulose), and mixtures of thereof. In preferred embodiments, the container of the device is prepared from non-dissolvable, non-bioerodible materials, which are referred to as "Ghost" materials. These materials are able to pass through the digestive system without erosion so that any hydrogel contained within the container will not come in contact with the biological host. Thus, even hydrogels of unknown toxicity profiles may be used in the preparation of the device.

The container desirably contains pores in order to allow both water penetration into the device and the release of the drug. In preferred embodiments, pore size within the container is restricted only in that the hydrogel is constrained from leaving the device through the pores. No pore design to control the osmotic pressure is required. The device container may contain pores over the entire container surface area or the pores may be contained to a specific region localized in proximity to the volume expandable hydrogel which is contained therein.

Appropriately sized pores of the container may be pre-existing. In such cases they would be made at time of manufacturing. For example, holes could be introduced into the container with a laser drill or the container could be fabricated from a porous sheet of thermoplastic polymer(s). Laser holes are commonly required in existing systems because the precise size of the hole is critical to the create precise back pressure in such devices and thereby control the total osmotic pressure and the delivery rate; however, the present invention is not so limited.

Alternatively, and preferably, pores may be formed in situ. In one such design, porosigens (pore forming agents) would be incorporated into the container, such as e.g., inorganic salts, such as alkali metals (e.g., NaCl, KCI, NaBr, $Na_2CO_3$, KCl, etc.); alkaline earth metals (e.g., calcium phosphate, calcium nitrate, calcium chloride, etc.); saccharides (e.g., glucose, sucrose, pentose, hexose, fructose, mannitol, manose, talose, sorbitol, etc.); and soluble polymers (e.g., polyethylene glycol (PEG), cellulosics; etc). Also, the porosigens could be environmentally sensitive to formation of pores at a desired site in the GI tract. Once the device is placed in the environment of use, the porosigens dissolve and form desired pores in the container. It should be clear that such pores could be uniformly or non-uniformly disposed throughout the container, that the pores could be of uniform or non-uniform size, and that such pores could desirably be formed only under specific conditions, thus adding yet additional dimensions of control to the chemo-mechanical system design.

In preferred embodiments, the hydrogel compartment is separated from the biologically active agent compartment of the container using a partition. The partition may be movable, that is, it may be displaced along the expansion front of the hydrogel as the hydrogel expands in response to an environmental stimuli. Alternatively, the partition may be fixed at one point within the device; however, it is sufficiently flexible so as to deform in response to the expanding hydrogel. In this respect, it is similar to a balloon or other such flexible membrane.

The partition may be permeable or impermeable to fluids depending upon whether it is desired to dilute or solubilize the biologically active agent with body fluids. In other embodiments, the partition may take the form of a layer of waxy polymer that melts at body temperature, or another hydrogel or superabsorbent hydrogel that will swell faster then the environmentally responsive, volume expandable hydrogel and will provide a water barrier.

In other embodiments, the device may be designed without any partition. The particle size of the environmentally responsive, volume expandable hydrogel is selected to be sufficiently large so as to minimize entrainment of the drug within hydrogel. Alternatively, the hydrogel in the form of a disk or monolith is well-suited for use in a partitionless device. In this case the swelling of the environmentally responsive, volume expandable hydrogel will form a squeezing action to expel the drug solution out of the orifice at the opposite side of the system device. A partitionless configuration is particularly preferred in drug formulations that do not interfere with the swelling stimuli.

The biologically active material or drug 24 may be any material approved for use in a particular diagnostic or treatment protocol. Classes of biologically active compounds which can be loaded into the second compartment 14 include, but are not limited to, prodrugs, antisense, oligonucleotides, DNA, antibodies, vaccines, other recombinant proteins, anti-AIDS substances, anti-cancer substances, antibiotics, immunosuppressants (e.g. cyclosporine) anti-viral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, genes and enzymes.

In some embodiments, the drug may be formulated as a liquid in either aqueous or oil phase. Alternatively, the drug may be formulated as a solid with or without solubilizers (agents that promote drug dissolution into the media) to control the dissolution rate of the drug in which case it may be desirable to transport water (or body fluids) into the drug compartment. Fluid transport will be driven by the osmotic gradient and/or controlled by the pore size in the container structure. It also may be established by incorporation of a semipermeable membrane into the container region defining the drug compartment. Alternatively, the osmotic gradient may be caused by the drug alone (i.e., it's charge, size), by osmotic agents, or by excipients.

If the drug is soluble it will dissolve and be available for delivery by the hydrogel at the appropriate site. Conversely, where the drug is insoluble or of low solubility, the solubility of the drug could be enhanced by the addition of solubilizing agents. Solubilizing agents include: soluble polymers (PEG, PEO, cellulosics), carbohydrates (mannitol, sorbitol, dextrane), low molecular weight molecules (small organic acids, organic salts, quaternary amines) surfactants (SDS, fatty acids, poloxamers) etc. These agents are mixed with the drug during or prior to device manufacturing. These excipients could be dry mixed with the drug or wet processed (spray drying, casting, granulation, lyophilization, direct compression or spheronization). In addition to the above-mentioned excipients, other pharmaceutical accepted excipients may be present for manufacturing and/or performance purposes. Excipients include binders (microcrystalline cellulose), plasticizers (PEG), buffering agents (sodium phosphate) and stabilizing agents (sugars).

Preferred crosslinked polymer networks for use in the device 10 of the invention are gels that are "responsive"— i.e., gels that, when challenged with an environmental condition, are affected by that environmental condition so as to cause the entire gel, or a component thereof, to undergo a volumetric change in which the gel expands from a less liquid-filled state or a dry state to a more liquid-filled state. The degree of volumetric change between unexpanded and expanded states of preferred responsive gels at their particular environmental transition region is quantitatively much greater than the volume change of the gel outside the environmental transition region. Suitable gels for use in the present invention may be a single material such as a single polymer network which meets the volumetric response requirement. The gel may also be a co-polymer, whether a random, alternating, graft or block co-polymer. Other suitable polymers include those which include those of known acceptable toxicity profile which meet the volume responsive requirement. The gel may also include two or more polymers, so long as the result is a physical polymer blend, wherein at least one polymer meets the volumetric response requirement. The gel may also be an interpenetrating polymer network (IPN) in which each polymer maintains its integrity.

The volume change of the entire gel, or a component thereof, may be either continuous or discontinuous. The crosslinked gels suitable for use in the invention may undergo a "discontinuous" volume change in which the transition from swollen to collapsed states, and back again, occurs over a small change in environmental condition, such as less than 1°/10° C. or ⅒ pH unit. It is preferred that the discontinuous volume change occur within a range of approximately 5° C. and one pH unit. Such gels are often called "phase-transition" gels (see, for example, Tanaka et al., *J. Chem. Phys.* 87(15), p.1392–4, 1987, which describes synthetic polymeric gels that undergo phase transitions). The crosslinked gels suitable for use in the invention may undergo a "continuous" volume change in which the transition from unexpanded to expanded states occurs over a larger change in environmental condition or over a greater period of time. A gel undergoing a continuous phase-transition may have a similar order of magnitude total volume change as a gel undergoing a discontinuous phase-transition. The volume transition may be either reversible or irreversible.

Hydrogels prepared for use in the apparatus of the invention, for example, the hydrogels reported in Example 2, were tested for toxicology in standard animal models. In all cases, initial toxicological evaluations demonstrated that the materials were safe. The results are reported in Table 1.

TABLE 1

Toxicological Evaluation Data for hydroxypropylcellulose crosslinked with multifunctional carboxylic acid

| Toxicological Test | Test Subject | Results |
| --- | --- | --- |
| Hemolysis Test | rabbit blood cells | negative |
| Cytotoxicity Test | rabbit fibroblast cells | negative |
| Mutagenicity Test | salmonella typhimurium | negative |
| Acute Study in Mice | single oral dose (25 mL/kg) | no toxicity |
| Acute Study in Mice | single IV dose (20 mL/kg) | no toxicity |

The drug could be delivered in a variety of ways, depending upon its solubility and physical state. For example a liquid dose could be administered as follows. Once the volume expandable hydrogel "senses" the right environment (i.e., pH) it starts to swell in a controlled rate. As a result of this swelling it operates as an actuator and expels the liquid drug/drug solution out to the environment at a controlled rate. A solid dose could be administered as follows. Once the device comes in contact with water or other body fluid, the drug compartment is filled with fluids at a known and, as described, potentially controlled rate as a result of pores or membrane included in the container. As a result the solid drug dissolves to form a solution that is contained within the device. Dosage proceeds is as described for liquid dose. Similarly, the drug dissolution rate is timed with the swelling rate, where only the needed amount of drug solution is present at any moment.

Figure 5A:
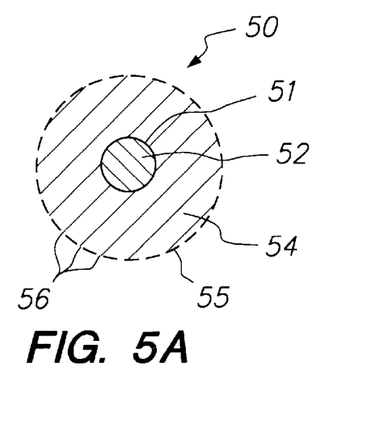
FIGS. 5A, 5B and 5C (collectively referred to herein as FIG. 5 represent cross-sectional views of several embodiments of the invention in which the hydrogel is of spherical form.

In other embodiments, the chemo-mechanical system may be configured as a spherical device. Referring to FIG. 5A, a spherical device 50 may include a core 51 comprising an environmentally responsive, volume expandable hydrogel 52 which is coated with a solid drug 54 mixed with or without another solubilizing excipient/s through granulation, coating apparatus, spray drying, or other similar system. The core 51/solid drug coating 54 are encompassed by a container 55 containing pores 56 as described hereinabove.

Figure 5B:
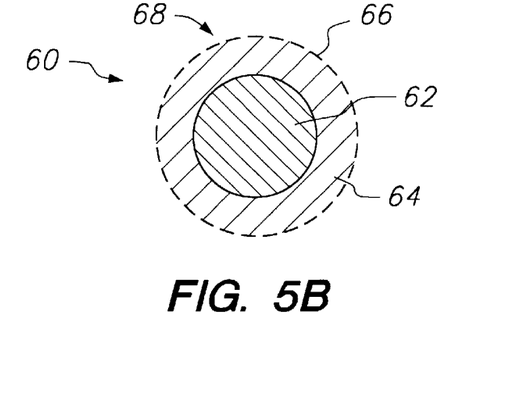

In other embodiments, as shown in FIG. 5B, a spherical device 60 could be made of a solid drug core 62 (mixed with or without another solubilizing excipient/s) surrounded by the environmentally responsive, volume expandable hydrogel 64. The solid drug core 62 and hydrogel 64 are encompassed by a container 66 containing pores 68 as described hereinabove.

Figure 5C:
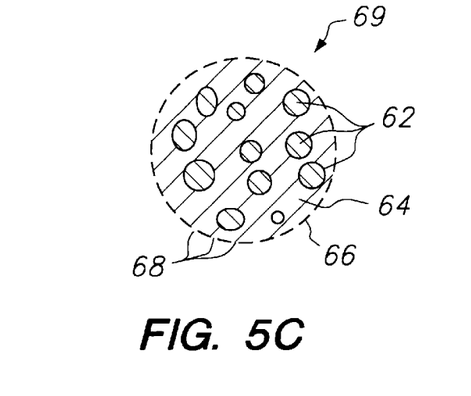

In other embodiments, as shown in FIG. 5C, the spherical device 69 could be made of a homogenous or heterogeneous mixture of volume responsive hydrogel beads 62 mixed with solid drug 64 (mixed with or without another solubilizing excipient/s). The solid drug core 62 and hydrogel 64 are encompassed by a container 66 containing pores 68 as described hereinabove.

It should be clear that the term "spherical" is used to describe a specific form, but is not intended to be restrictive. For example, one skilled in the art could imagine reasons why an ovoid, cylinder, or other complex three-dimensional shape might be desirable and such would be readily designed and manufactured.

Figure 6:
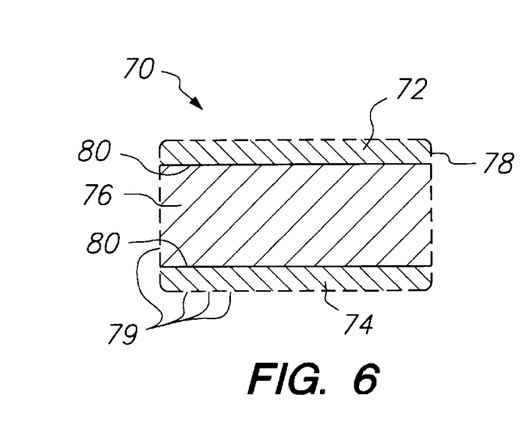
FIG. 6 is a cross-sectional view of a third embodiment of the invention disclosed herein.
Figure 7:
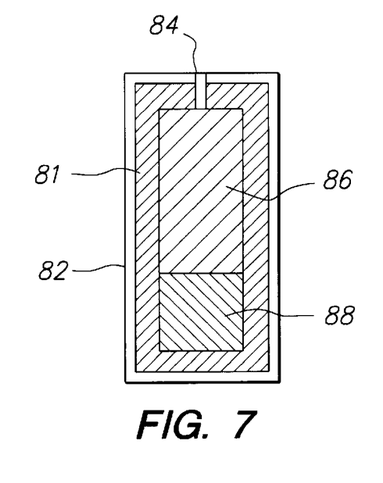
FIG. 7 is a cross-sectional view of another embodiment of the invention disclosed herein.

In another embodiment of the invention, the chemomechanical system may take the form of a three-compartment sandwich device 70, as shown in FIG. 6. In this embodiment, outer top and bottom components of the device, 72 and 74, respectively, are made of an environmentally responsive, volume expandable hydrogel. A core 76 of the device is made of the drug in a solid form. A device container 78 including pores 79 could be made as described above. The device may include partitions 80 located between the hydrogel layers 72, 74 and the drug core 76. Alternatively, the device may be made from two discs of environmentally responsive, volume expandable hydrogel, which would not require the use of a partition. Once the device is come in contact with bodily fluids the drug will be solubilized as described above.

The description of this device as a sandwich is not intended to be restrictive. For example, one skilled in the art could imagine implementation of outer hydrogel layers of differing thicknesses, multi-layer structures, use of different environmentally responsive volume expandable hydrogel for the top and bottom components (e.g., different hydrogels, different porosigens, etc.). It is further contemplated to use a multi-layer version of the for delivery of different drugs and/or drugs in a pulsatile form. These and other implementing details are contemplated as within the scope of the invention.

Figure 8:
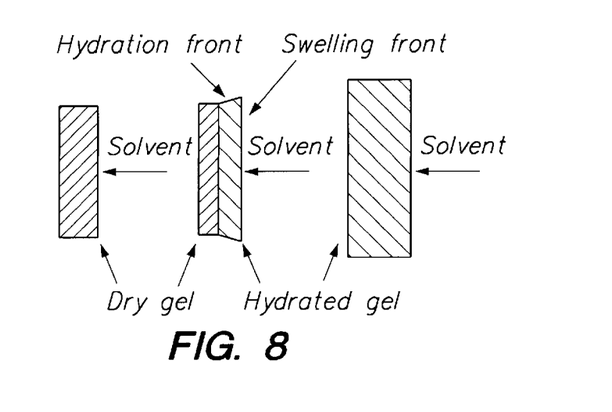
FIG. 8 is an illustration of the moving front in a dried gel.

Another embodiment of the invention is shown in FIG. 8. A rigid inner porous or perforated wall 81 is covered with an outer biocompatible, flexible membrane 82. The inner wall provides support allowing the device to retain its shape. The outer membrane provides biocompatibility, and could be permeable to both the chemical stimuli triggering volume expansion and the drug. Alternatively, the drug will be delivered either through orifice(s) 84 or through the membrane 82. The drug and the hydrogel are housed in compartments 86 and 88, respectively. The membrane 82 could be a dialysis membrane (membrane with a certain molecular weight cut-off). Materials of construction for such a membrane could be: cellulose, polysulfone, polymethylmethacrylate. Other membrane could be, by way of example only, ethylene vinylacetate, polyptropylene, polyvinylidene, difluoride, polycarbonate, and other water soluble polymers such as: polyhydroxyethyl methacrylate, polyvinylpirrolidone, polyacrylamide.

The swelling kinetics of the present system has been investigated and is disclosed hereinbelow. The investigation demonstrates, among other things, that the physical structure and geometry of the hydrogel component has an effect on the swelling kinetics and hence the release rates of the drug. For example, hydrogel beads exhibit a non-linear swelling rate in Simulated Gastrointestinal Fluid, whereas hydrogel disks exhibit a linear swelling rate. This knowledge may be used as a guide to one skilled in the art in selecting from the variety of device structures in order to provide the desired release kinetics of the drug of interest.

Volumetric changes in aqueous gels are driven primarily by four fundamental forces: ionic, hydrophobic, hydrogen bonding and van der Waals bonding interactions, either alone or in combination. Each of these interactions may be independently responsible for a volume transition in preferred gels of the invention. Each of these fundamental forces is most strongly affected by a particular trigger. Changes in solvent concentration most strongly affect the van der Waals interaction; changes in temperature most strongly affect hydrophobic interactions and hydrogen bonding; and changes in pH and ion concentration most strongly affect ionic interactions. The volumetric changes of the hydrogels described herein result from competition between intermolecular forces, usually electrostatic in nature, that act to expand the polymer network; and at least one attractive force that acts to shrink it.

The swelling of hydrogels is a complicated phenomenon that consists of several separate but interrelated physical processes: (1) collective diffusion of the network, (2) diffusion of solvent into the network, (3) diffusion of ions into the network, and (4) plastification of the dried gel. The rate of swelling is controlled by the slowest of these processes; however, the relative importance varies at different stages of hydration.

When a dried gel in the glassy state is placed in a solvent, it starts swelling at the surface. The moving front result, the swelling front where the hydrated gel contacts the solvent, and the hydration front where the dry gel becomes wet, as is illustrated in FIG. 8. This phenomenon allows one to treat the problem of a swelling disc as one-dimensional.

Collective diffusion describes the elastic behavior of the gel network. Under a theory of gel swelling in terms of network elasticity, the gel is represented by a continuum model with the displacement from equilibrium at position r, defined as u(r). The system obeys a diffusion equation:

$$\frac{\partial u}{\partial t} = D\nabla^2 u$$

where D is the diffusion coefficient expressed in terms of the longitudinal modulus E and the network-solvent friction coefficient fD=E/f. The longitudinal modulus can in turn be obtained from the bulk (K) and shear moduli ($\mu$): E=K+4$\mu$/3. These depend on the chain-solvent interaction (hydrophobicity), degree of crosslinking, degree of ionization and the degree of hydrogen bonding. The latter two are dependent on the solvent pH. For example, the shear modulus is related to the effective crosslink density $\rho_x$ and the volume fraction of the polymer $\phi$ though, $$\mu = \rho_x \phi^{1/3} RT$$

The solutions reach equilibrium exponentially with a time constant $\tau \propto a^2/D$, where a is the gel size. The solution is exact for spheres; it is slightly more complicated for other shapes. Thus, one can control the rate of swelling by changing the size of the gel particles.

Collective diffusion describes the kinetics of a wet-to-wet transition (swelling of an already hydrated gel). It is the rate limiting process when the solvent access is not restricted, i.e., when the gel is swollen. The solvent diffusion can be the rate limiting step when the gel is almost dry. In this case, Fickian diffusion dynamics governs the swelling. For a spherical gel, the kinetics is described by the equation:

$$\frac{H}{H_{eq}} = \begin{cases} 6\left(\frac{Dt}{\pi r_o^2}\right)^{\frac{1}{2}} - 3\frac{Dt}{r_o^2} & \frac{H}{H_{eq}} < 0.5 \\ 1 - \frac{6}{\pi^2}\exp\left(-\frac{-\pi^2 Dt}{r_o^2}\right) \end{cases}$$

otherwise where H is the hydration ration (weight of water/total weight), $H_{eq}$ is the equilibrium hydration, and $r_o$ is the initial radius. Here, D is the chemical diffusion coefficient of solvent within the network. It can be controlled by changing the solvent-polymer interaction and/or the gel porosity. The diffusion of ions into the gel follows similar dynamics. The diffusion coefficient should be different because there are interactions of the ions with the charges on the network. Therefor this process is pH dependent.

Given an adequate supply of solvent, the plastification of the dry gel is a linear ($0^{th}$ order) process. The rate depends on the area exposed to water. For a gel disc, that area remains constant as the hydration front progresses.

As mentioned above, it is the interaction of all these processes that governs the swelling kinetics. This interaction is governed by the parameter called a diffusional Deborah number, De, defined as, $$De = \tau_{rel}/\tau_D$$

where $r_{rel}$ is the characteristic relaxation time and $\tau_D$ is the characteristic solvent diffusion time:

$$\tau_D = a^2/D_s$$

α being the sample size and $D_s$ being the diffusion coefficient of the solvent. When De=1, $zero^{th}$ order diffusion may be expected. It is therefore advantageous to choose gel parameters to approach this condition.

Any particular application, such as pH responsive swelling of a hydrogel places some constraints on the gel characteristics. Nevertheless, there are plenty of parameters that can be freely adjusted to obtain the desired kinetic behavior. By changing the gel hydrophobicity, the polymer-solvent interactions are affected, influencing the elastic moduli, the solvent diffusion rate and the plastification rate. Changing the crosslink level affects the phenomena, but to a different degree. The amount of charged groups is related to the ion diffusion and also affects the pH response. The carboxyl groups (and other polar, hydrogen bonding groups) also play another role by hydrogen bonding the gel at low pH values, thus increasing the pH responsiveness. Finally, the gel particle size and shape is a factor in determining the overall relaxation time. Thus, the gel designer has a lot of room to tailor the gel behavior to the particular demands of the application.

Thus, a gel whose volume change is governed by ionic interactions would include components that are weakly acidic and weakly basic, such as poly(methylmethacrylate)/dimethylaminoethyl methacrylate (see, for example, Siegel et al., *Macromolecules* 21(3254), 1988) and cellulose ethers such as HPC crosslinked by methods described herein. Gels of this type are sensitive to pH (see Example 1).

Gels whose volume change is governed by hydrogen bonding will collapse with a decrease in temperature and are exemplified by interpenetrating polymers that comprise acrylamide as one polymer, acrylic acid as the other polymer, and water as the liquid medium. Gels whose volume change is governed by hydrophobic interactions will collapse when challenged with an increase in temperature and are exemplified by N-isopropylacrylamide. Gels whose volume change is governed by van der Waals interactions will behave similarly to those governed by hydrophobic interactions.

Gels may be formulated in which the volume change is governed by more than one fundamental force. In particular, gels consisting of copolymers of positively and negatively charged groups meet this requirement. In these gels, polymer segments interact with each other through ionic interactions and hydrogen bonding. The combination of these forces results in the existence of several pH-driven phases (see, for example, Annaka et al, *Nature* 355(430), 1992, incorporated herein by reference).

Polymer gel compositions of the present invention are particularly useful for oral delivery compositions. It should also be noted that the device 10 could be located outside the body for other drug delivery applications such as cyclic infusions or transdermal delivery. For example, polymer gel networks of the present invention that are responsive to changes in pH or the other triggers discussed above can be utilized to effect controlled release of compounds at specific locations along the gastrointestinal tract. Similarly, polymer gel networks that are responsive to changes in pH can be utilized, for example, to effect controlled release of substances into only one of a cow's stomachs.

Without wishing to be bound by any theory, a cellulose ether gel such as hydroxypropylcellulose (HPC) with a lower critical solution temperature (LCST) near body temperature (e.g. 42° C.) should have its LCST shifted to a lower temperature at lower pH. This is because very few —COOH and/or —OH groups are ionized at low pH and the gel would tend to have a reduced hydrophilicity. At higher pH, many —COOH and/or —OH groups will be ionized and the LCST is shifted to a higher temperature due to increased hydrophilicity. Around body temperature, the gel is therefore very sensitive to pH change and would be collapsed at low pH (i.e. that of the stomach, where the drug would be retained in the device 10) and expanded at higher pH (i.e. that of the intestine, where the polymer gel network would expand and release the drug). A responsive gel may be made from starting materials (i.e. cellulose ethers of various configurations) that vary in their hydrophobic/hydrophilic nature when ionized, so that the methods described herein may be used to make a reversibly responsive, pH-sensitive gel with an LCST designed to match the body temperature of a desired subject. The LCST of preferred cellulose ethers is well known and can be easily determined and verified. Exemplary LCST's (°C.) are 49° (MEC); 42°–46° (HPC); 59° (methyl(hydroxypropyl)cellulose: HPMC); 60° methyl (hydroxyethyl)cellulose; and 55°–70° (ethyl(hydroxyethyl) cellulose).

The device 10 of the present invention provides better control of drug release than prior art, osmotic-type pump systems. The prior art devices release drugs solely as a function of time after ingestion rather than upon the encounter of an environmental condition such as pH. An example is U.S. Pat. No. 5,413,572 to Wang et al. which suggests the use of a hydrogel which expands upon contact with water whose expansion then disgorges a drug. While one or more of the hydrogels contemplated by Wang might exhibit a volume change in response to an environmental condition, this property is neither utilized nor appreciated by Wang et al. The Wang et al. hydrogels begin expanding upon contact with water immediately upon ingestion and thus the drug is continuously released. The hydrogels suitable for use in the device of the invention, on the other hand, expand only upon the achievement of a selected environmental condition such as a preselected narrow pH range or other disclosed triggers.

The following example teaches the preparation of a pH responsive gel suitable for use in the apparatus of the invention.

EXAMPLE 1

Preparation of pH and Temperature Sensitive Hydroxypropylcellulose Gel with Adipoyl Chloride Reagent Exactly 50 mL of N-methyl pyrolidone (Fisher Scientific, Catalog No. 03688-4) was added to 5 grams of hydroxypropyl cellulose (Aqualon, Klucel 99-EF NF). The two materials were mixed on a magnetic stirrer for about 2 hours, while covered, to achieve a clear and colorless solution. This solution was then placed in a refrigerator for about 1 hour in order to achieve a solution temperature of 4°–8° C. To this solution, while stirring, 1 mL of cold (2°–8° C.) adipoyl chloride (Aldrich, Cat. No. 16,521-2) was added, and the resulting solution allowed to stir for 1 minute. After stirring, this solution was allowed to gel for eight hours.

A general protocol for forming a polymer network suitable for use in the present invention using a crosslinkable polymer includes the steps of dissolving the polymer(s) in a suitable solvent and allowing the polymer(s) and solvent to mix. A crosslinking agent is then added to the polymer solution, and the solution and crosslinker are further mixed together. The resulting solution may be poured into a solid mold (e.g. between two glass plates), and the crosslinking reaction carried out. Examples of backbone polymers include hydroxypropyl cellulose (HPC), hydroxypropyl methyl cellulose (HPMC) and hydroxypropyl starch (HPStarch). Examples of multifunctional carboxylic acid crosslinkers include acyl halide derivatives of adipic acid, sebacic acid and succinic acid.

In an exemplary sequence, a chemical crosslinking reaction is carried out in the homogenous polymer state at room temperature to form a certain amount of polymer network. Total crosslinking time will vary but is generally less than 24 hours. The network is then removed from its mold, and repeatedly washed to leach out any leachable material present in the network. In principle, a polymer network can be made from any polymer with side groups that can react with a di- or multi-functional crosslinking molecule. Temperature and/or pH responsiveness, strength, degree of swelling and swelling rate are designed into the hydrogels by choosing the appropriate backbone polymer, crosslinker, crosslinker level and fabrication methodology.

The polymer solution may also be formed into beads or spheres using crosslinking in a non-solid mold where the reacting solution (polymer, crosslinker and catalyst, if needed) is dispersed in a non-solvent to form a droplet. The solution reacts within the droplet to form a bead. In this method, the non-solvent may be considered to be a "mold" for polymer network droplets.

U.S. Pat. No. 3,208,994 to Flodin et al., incorporated herein by reference, generally discloses methods of preparing polysaccharide gel beads using suspension crosslinking. One introduces a water soluble polysaccharide and crosslinker into a suspension medium under agitation to obtain suspended drops of the polysaccharide solution. Another method of preparing gel beads uses inverse emulsion polymerization, in which a monomer solution is introduced into a dispersion solvent to form monomer droplets and polymerization is initiated to form polymer gel beads (see, for example, Hirose et al., *Macromolecules* 20(1342), 1987, incorporated herein by reference). Preferably, an aqueous cellulose ether solution, a non-polar saturated hydrocarbon solvent, and a crosslinker are provided and admixed to form a two-phase system. The two-phase system is agitated sufficiently to form droplets of aqueous cellulose ether solution in the two-phase system. The agitation of the two-phase system is maintained to form crosslinked cellulose ether gel beads and the crosslinked cellulose ether gel beads are thereafter recovered from the two-phase system.

Polymer networks of the invention also may consist, in whole or in part, of polymers made by copolymerization/crosslinking of monofunctional and polyfunctional polymerizable monomers.

A preferred method for making gels from cellulose ethers involves dissolving a sample of cellulose ether such as HPC or HPMC in an anhydrous solvent that does not contain active hydrogen, such as for example N-methyl pyrolidone (21 C.F.R. 176.300), dimethylsulfoxide (DMSO), dimethylformamide (DMF), methylethylketone (MEK), tetrahydrofuran (THF), and the like. The concentration of polymer in the solution may range from about 5–20% by weight of polymer per volume of solution, with a preferred concentration primarily a function of the kind of polymer used in the synthesis. The molecular weight of the cellulose ether should be at least about 20,000. Preferred molecular weights range from about 75,000 to about 150,000. The higher the molecular weight of the polymer, the sharper will be the volume change of the resulting responsive gel. This is because a higher molecular weight will result in formation of a more consistent three-dimensional polymer network. Molecular weights may range up to 1,000,000 or more although it will be understood that viscosity effects will place an upper limit on the molecular weight of the polymer starting material. Those having ordinary skill in the art may readily determine using the methods described herein the extent to which viscosity constraints interfere with the gel formation process and/or prevent the crosslinker from mixing with the polymer.

When synthesizing gels suitable for use with the invention with a crosslinker reagent that is a dicarboxylic acid, azeotropic distillation is a preferred method. A first solvent such as DMSO is added to a distillation flask containing the polymer and crosslinker reagents. Both are mixed to achieve a clear solution. To this solution, a small amount (several hundred $\mu L$) of an acidified solution of first solvent is added, followed by the addition of a second solvent (e.g. toluene). This solution is allowed to react under azeotropic distillation until a gel forms in the flask. The gel is then removed and placed in an excess of deionized water. The water is removed and excess primary alcohol (e.g. methanol) is added to remove excess solvent. The gel is washed and then dried in a desiccator.

Synthesis of gels using acyl halide derivatives of dicarboxylic acids generally occurs as follows: While stirring the cellulose ether polymer solution under anhydrous conditions, the solution is cooled slightly below room temperature (in some embodiments to between about 10°–20° C.) and a cold solution (in some embodiments between about 2°–8° C.) of a preferred acyl halide derivative of a multifunctional carboxylic acid is added as crosslinker to the polymer solution. This solution is stirred and then allowed to sit until gelation has occurred. Gelation time will necessarily vary and may occur within about 2 hours (e.g. for HPC) or as long as 24 hours (e.g. for HPMC). The polymer/crosslinker weight ratio is between about 12/1 and 8/1. The lower the ratio, the more highly crosslinked the resulting gel will be.

The reaction will not always produce polymer/ crosslinker/polymer covalent couplings, and a number of incomplete crosslinks will occur that will leave one end of the acid chloride group unreacted. After the crosslinking reaction, any unreacted acid chloride is quantitatively reacted with water to produce a carboxylic acid group. Carboxylic acid groups in the polymer network will provide a pH- and temperature-responsive gel (see Example 1).

Alternatively, if it is desired to produce a gel which has basic (amine) groups rather than acid groups, this may be achieved for example by allowing the acyl halide, cellulose ether reaction product to react with a diamine such as ethylenediamine or hexamethylenediamine (21 C.F.R. 175.300 (b)(3) (xxxii) to produce an amine-terminated amide. The amine-terminated amide will survive the workup. These amine groups will cause the gel to be pH and temperature responsive in a range different from the acid group-containing gel.

After the gel is formed, destruction of any remaining acid chloride groups is carried out by soaking the gel in distilled water for about 12 hours. Solvent is then removed by soaking the gel in an alcohol (e.g. methanol, ethanol, and the like) for at least several hours so that the methanol can diffuse into the gel and the solvent can diffuse out of the gel. After several hours, the wash is drained off. This process is repeated at least 4–5 times. The gel is then washed 4–5 times with distilled water while it is being heated to between about 60°–80° C. for about 2 hours. Heating drives off any remaining alcohol, leaving gel and water. The process is repeated at least 3–5 times until the gel appears opaque at the elevated temperature. This opacity signifies that the gel has undergone a volumetric change at a lower critical solution temperature (LCST), and therefore that the gel has temperature responsive characteristics. For HPC, the LCST is between 42° and 46° C. The degree of responsiveness to pH may be assayed using the device and procedures given in Example 1.

Persons having ordinary skill in the art may readily determine if a particular polymer material is capable of forming a polymer gel network by following the synthesis procedures described herein. Moreover, methods to determine the degree of crosslinking are conventional and are described, for example, by Peppas et al. (eds) in "Hydrogels in Medicine and Pharmacy" Vol. 1, CRC Press, Boca Raton, Fla., 1986. In operation, the first compartment 12 of the device 10 is loaded with a suitable hydrogel, as described above. A desired biologically active material or drug 24 is loaded into the second compartment 14. The thus loaded device is ingested and fluids in the environment pass through the screen or membrane 18 to interact with the hydrogel 22. When, for example, the pH is high (and only in that circumstance), the hydrogel 22 will undergo a volume expansion moving the moveable partition 16 to expel the drug 24 through the orifice 20. After drug 24 release, the device 10 will continue its passage through the system with subsequent natural elimination from the system.

EXAMPLE 2

This example investigates the swelling characteristics of hydrogels suitable for use in the apparatus of the invention.

Swelling is an attribute related to the suitability of the hydrogel for use in the apparatus of the invention. Swelling is determined by the mass of aqueous solution uptake per gram of gel and is approximated by the equation: Methods of measuring the swell factor involve hydrating a known mass of dry hydrogel in a particulate or disc form and determining the mass of the hydrated hydrogel after a predetermined amount of time. Table 2 summarizes the swelling characteristics of a variety of hydrogels at low and physiological pH. Swelling measurements are taken at 24 hours. HPC and HPMC hydrogels demonstrated significant pH responsiveness, whereas HPStarch hydrogels had a lesser response.

TABLE 2

Swelling Characteristics of Various Hydrogels

| polymer | crosslink (ml) | swelling at pH 2.2 | swelling at pH 7.4 | pH 7.4 swell/ pH 2.2 swell |
|---|---|---|---|---|
| HPC | adipoyl Cl (1) | 1.45 | 5.45 | 3.76 |
| | adipoyl Cl (0.5) | 0.81 | 3.76 | 4.64 |
| | adipoyl Cl (0.4) | 0.97 | 5.18 | 5.33 |
| | sebacoyl Cl (0.5) | 0.82 | 2.3 | 2.80 |
| | sebacoyl Cl (0.4) | 1.11 | 3.05 | 2.76 |
| HPMC | adipoyl Cl (1) | 4.4 | 25.13 | 6.23 |
| | sebacoyl Cl (1) | 1.36 | 8.97 | 6.60 |
| | sebacoyl Cl (0.85) | 1.48 | 10.58 | 7.13 |
| HPStarch | adipoyl Cl (1.75) | 8.21 | 12.35 | 1.5 |
| | sebacoyl Cl (1.75) | 5.59 | 10.03 | 1.8 |
| | succinyl Cl (1.75) | 11.6 | n/a | n/a |

EXAMPLE 3

This example demonstrates the pH response of HPC hydrogel crosslinked with adipic acid.

Gels exhibiting a swell curve with minimal response at pH<5.0 and a significant response for pH>5.0 are considered suitable for intestinal delivery applications. Swell response over pH is an indication of such a response.

A weighed amount of gel particles having a size greater than 600 microns were placed into a range of citric acid buffers (pH of ca. 1.0, 2.2, 4.0, 5.1, 6.0, 7.0, 7.4) with Simulated Gastric Fluid (SGF) and Simulated Intestinal Fluid (SIF) at the pH extremes. The citric phosphate buffers provided a complete range of pH values with minimal changes to ionic strength.

Figure 9:
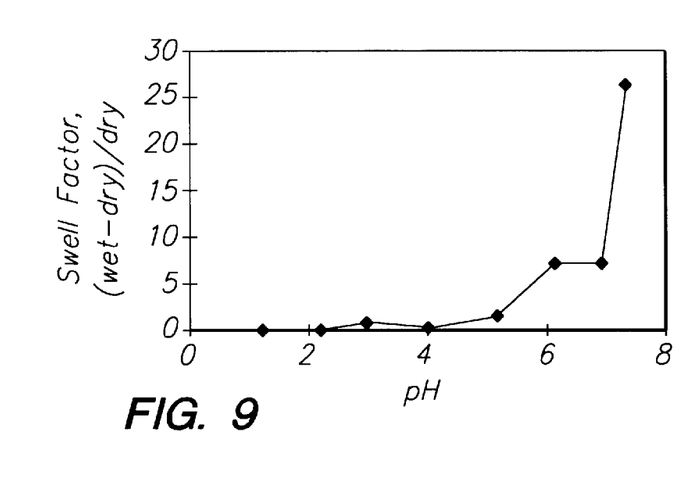
FIG. 9 is a pH response curve for an HPCAA hydrogel at 37° C.

Particles were placed in solution and allowed to equilibrate for 24 hours. The gels were then vacuum filtered using PTFE filter paper and wet weights were obtained. AT 37° C., the HPC hydrogel crosslinked with adipic acid (HPCAA) exhibited nearly ideal results with zero water absorbance at pH<5.0, moderate swelling for 5<pH<7 and over 20 fold swelling for pH>7. Results are shown in FIG. 9.

EXAMPLE 4

This example investigates the effects of hydrogel geometry and size on the rate of hydrogel swelling.

Controlling the rate of swelling by selective use of hydrogel compositions and geometries is desirable. The control of hydrogel expansion by the hydrogel itself permits the design of apparatuses with specific expansion and delivery properties.

Two sets of experiments were conducted. The first examined the swelling characteristics of dry 600 micron gel particles. The second examined the swelling characteristics of solid gel discs which were hydrated, but in a collapsed state.

Figure 10:
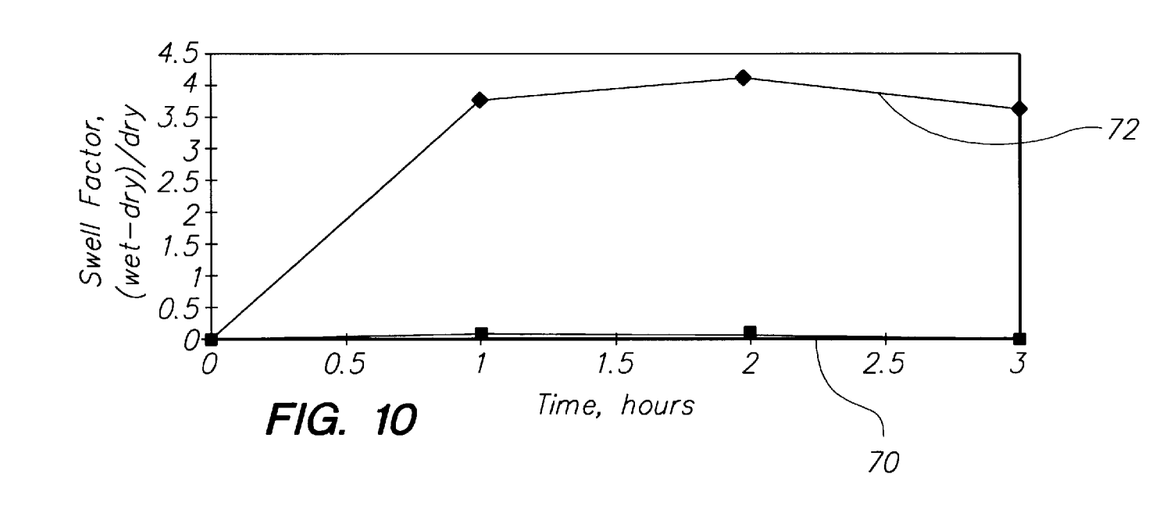
FIG. 10 plot of gel volume v. time for an HPCAA hydrogel at 37° C. in a Simulated Gastric Fluid (a) and in a Simulated Intestinal Fluid (b)

Dry particle swell rate was determined by allowing HPCAA gel particles (600 micron) to swell at 37° C. in a disposable cuvette. The height of the hydrated gel was recorded hourly to determine the volume change. Change in volume was plotted against time and presented in FIG. 10. Curve 70 represents swelling in SGF and curve 72 represents swelling of the hydrogel in SIF. The hydrogel particles reached maximum swell in SIF within an hour of exposure to the aqueous media and thereafter leveled off.

Figure 11:
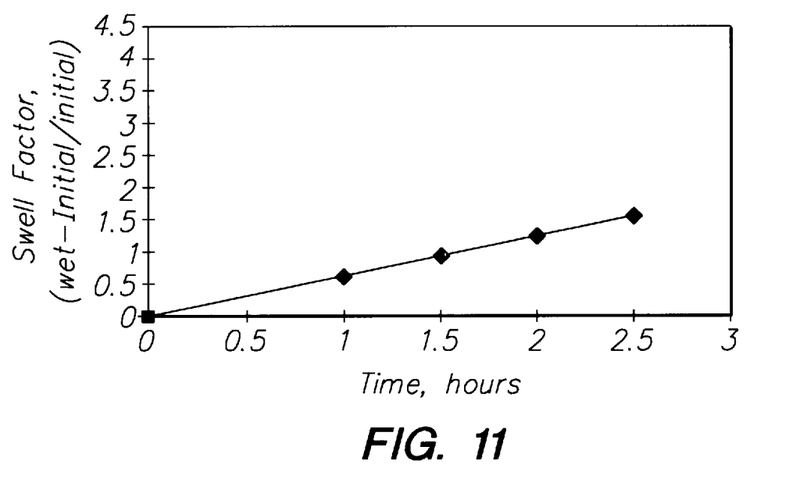
FIG. 11 is a plot of swell factor v. time for a hydrated HPCAA disc in SIF at 37° C.

The kinetics of swelling for hydrated solid HPCAA disks were determined. The discs were hydrated in SGF, bringing the hydrogel into a collapsed states. The collapsed, hydrated gels were placed into SIF and analyzed for solution uptake gravimetrically. The swell factor (hydrated volume-initial volume/initial volume) is plotted as a function of time in FIG. 11 and demonstrates a near zero order swelling rate.

Figure 12:
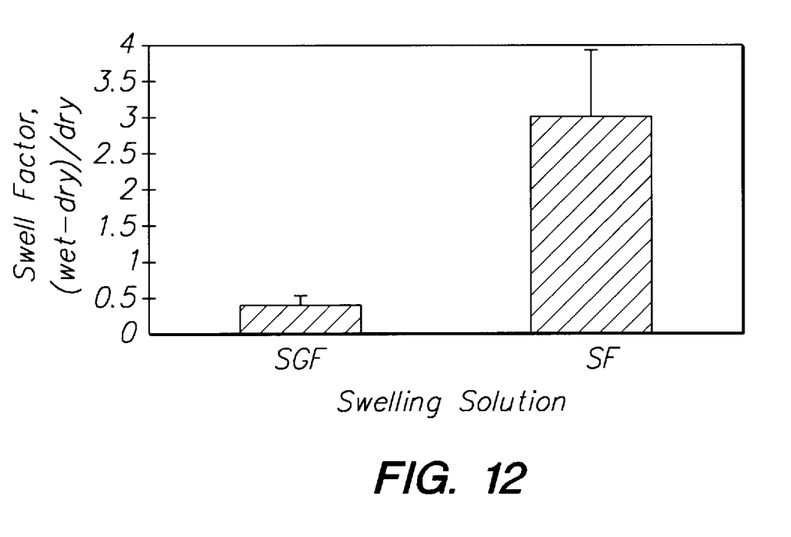
FIG. 12 represents the pH response at 37° C. of a hydrogel disc dried at 60° C.

A further study of swelling factors using hydrogel discs dried at 60° C. has been undertaken. Dried hydrogel discs are preferably from a manufacturing standpoint and it is desirable to demonstrate similar swelling kinetics from such a system. The pH response of such a disc is shown in FIG. 12.

EXAMPLE 5

This example demonstrates the ability of a hydrogel to swell under pressure, i.e., the expansion force exerted by the hydrogel upon swelling.

A hydrogel sample (e.g., HPCAA) is placed in a 0.15M NaCl solution and a series of weights of increasing value were placed on top of the hydrogel sample. The uptake of NaCl solution was measured and the uptake (expressed as a swell factor) was plotted against the log of the applied pressure, as is shown in FIG. 4. The linear relationship observed was used to estimate the pressure required to prevent uptake of solution, e.g., expansion force. In order to calculate expansion force, the material being evaluated should reach equilibrium swelling. In FIG. 4, HPCAA has not reached equilibrium, however, it can be noted that the expansion of the hydrogel is limited with higher pressure at early time points but that as time progresses, the hydrogel is able to expand and take up more solution. The hydrogel eventually reaches free swell volume, that is, the volume to which it swells when no pressure is applied. The ability to expand to free swell volume was observed up to a pressure of 0.6 ATM.

EXAMPLE 6

This example describes the preparation of an apparatus of the invention and demonstration of delivery of a substance therefrom.

A system was designed and constructed to demonstrate the principles of the apparatus of the invention. The design was cylindrical having a height of approximately 3.5 cm and a diameter of 2.5 cm. A 100 mesh stainless steel screen covered the bottom of the cylinder and provided access to solution. The bottom of the demonstration unit was covered with approximately one gram of particulate HPCAA hydrogel. A solid partition was placed on top of the hydrogel to serve as a barrier between the hydrogel and the substance to be delivered. The substance to be delivered was a viscous carbopol gel. A cover was attached to the cylinder flush with the carbopol gel and a hole was punched in the top. The system was then placed in an aqueous solution and the mass of carbopol emitted was plotted against time to obtain the release kinetics. Performance of this system provided zero order release over 24 hours.

A similar study was conducted using a hydrophobic mixture of petrolatum and mineral oil as the substance to be delivered. The system containing the material was placed into PBS and the mass of material emitted was plotted against time. A graph of the release kinetics is shown in FIG. 3. Delivery of a lipophilic material into a hydrophilic environment demonstrates the superior performance of the device as a means for delivery in a biological system, regardless of the physiochemical properties of the substance being delivered.

Another experiment was conducted to demonstrate the ability of the pH responsive HPCAA hydrogel system to selectively deliver at intestinal pH. The demonstration unit described above was charged with carbopol gel and was initially placed into a pH 2.2 buffer solution. After one and one half hours, the system was removed and placed into a pH 7.5 buffer system. Release of carbopol over time was plotted in FIG. 2 and demonstrates selective delivery to a neutral environment.

EXAMPLE 7

This example demonstrates systematic approach to developing a device for delivery into a biological system with acceptable performance criteria.

Figure 13:
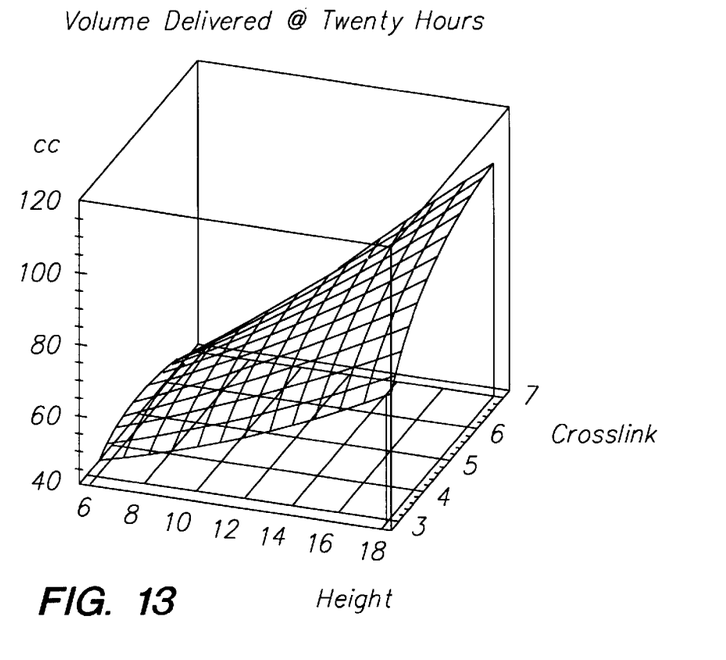
FIG. 13 is a response surface plot to optimize delivered volume from an apparatus of the invention.
Figure 14:
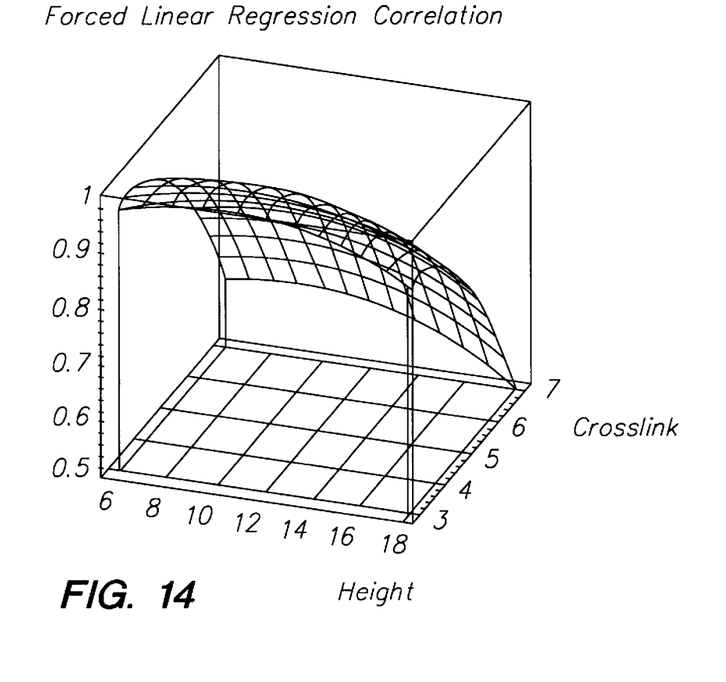
FIG. 14 is a response surface plot to optimize linearity of delivery from an apparatus of the invention.

The goal is to optimize the delivery of 1 mL of a substance as a function of hydrogel height and degree of crosslinking. Response surface plots are shown in FIG. 13 and FIG. 14. A working system may fabricated to have acceptable performance criteria based upon these response surface plots. This demonstrates the versatility of the design system to control hydrogel response to fit a particular system constraints.

Figure 15:
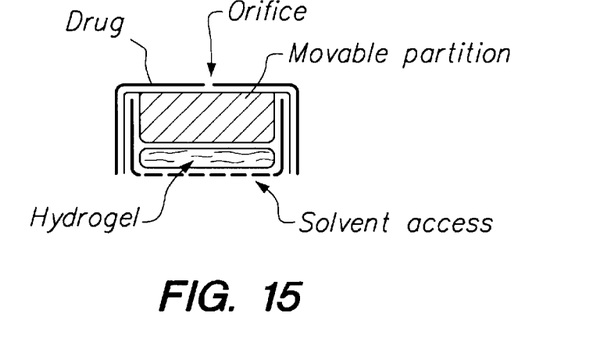
FIG. 15 is a schematic illustration of an apparatus of the invention.
Figure 16:
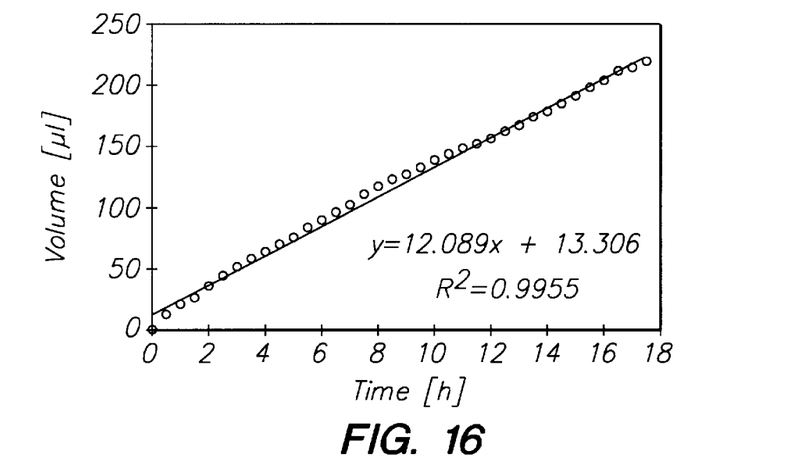
FIG. 16 is a plot of released volume v. time for release of a model substance from the apparatus of the invention.

Dimensional constraints. The desirability of reducing the size of the device was identified. Dimensional constraints of an intermediate size device were defined as having a height of 1.5 cm and a width of 0.7 cm. The volume system thus defined is approximately 0.6 mL. Prototypes developed to meet this dimensional constraint are shown schematically in FIG. 15. The device was evaluated for deliverable volume and linearity using various conformations and types of hydrogels as described above in Examples 2–6. Kinetic release curves from such a HPCAA prototype device is shown in FIG. 16 and demonstrates zero order release of 180 µL volume over a 24 hour period.

EXAMPLE 8

This example demonstrates delivery of a pharmaceutically active materials from an apparatus of the invention.

Figure 17:
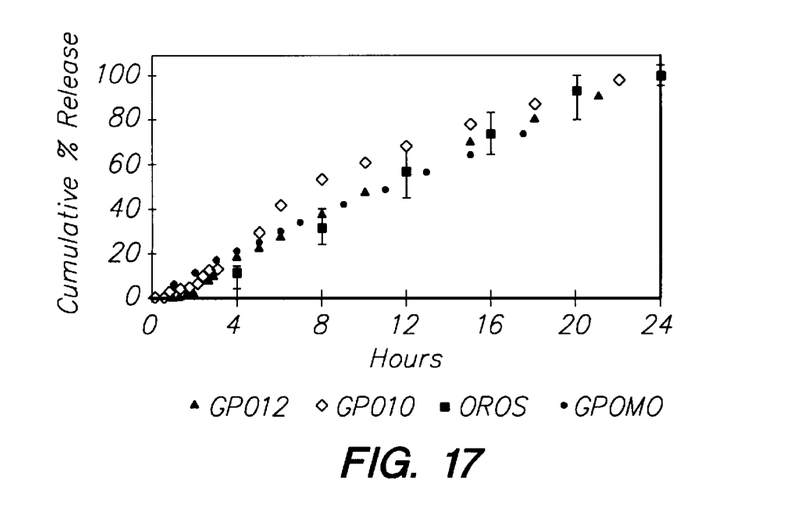
FIG. 17 is a plot of cumulative release v. time for release of nifedipine from the apparatus of the invention vs. An osmotically driven device made by Alza Co. (OROS®).

The device described in Example 7 was used to demonstrate controlled release of nifedipine. This compound was chosen because of its lipophilic character, and demonstrated commercial acceptance in a controlled release product. The nifedipine was formulated in a glycerol vehicle and was charged into the apparatus described in Example 7. A variety of hydrogel formulations were used to demonstrate release properties, which are designated by "GP" in FIG. 17. The apparatus was then placed into and SIF solution and allowed to deliver. The released nifedipine was collected at regular time intervals over six hours and assayed for concentration. Cumulative release normalized to percent of extrapolated nifedipine delivered in 24 hours was plotted against time and is shown in FIG. 17 as a plot of data points 150 having the "GP" designation. This release kinetics were compared to a release from a commercially available product, Procardia/Adalat table shown as curve 160 in FIG. 17, designated by "OROS" designation. Similar release profiles were obtained.

It will be appreciated by those skilled in the art that other embodiments of the invention are within the scope of the claims. For example, responsive hydrogels may provide the motive force on the plunger of a syringe-like device to provide an external continuous IV/IM/SQ infusion. Similarly, such a device can be implemented within the body to provide controlled release of a suitable drug.

What is claimed is:

1. Apparatus for controlled delivery of a biologically active compound to a biological environment comprising:
   a container comprised of a single member or two mated members, the container defining first and second compartments and comprising pores in at least a portion of the container defining the first compartment,
   the first compartment containing a polymer gel network which undergoes a volume expansion in response to an environmental condition which varies in the biological environment,
   the second compartment containing an effective amount of a biologically active compound and including at least one passageway communicating with the biological environment,
   whereupon volume expansion of the polymer gel network causes the biologically active compound to be discharged into the biological environment through the passageway.

2. Apparatus for controlled delivery of a biologically active compound to a biological environment comprising:
   a container comprising pores in at least a portion of the container;
   a first compartment within the container containing a polymer gel network which undergoes a volume expansion in response to an environmental condition which varies in the biological environment;
   a second compartment containing an effective amount of a biologically active compound and including at least one passageway communicating with the biological environment, the second compartment disposed within the first compartment;
   whereupon volume expansion of the polymer gel network causes the biologically active compound to be discharged into the biological environment through the passageway.

3. Apparatus for controlled delivery of a biologically active compound to a biological environment comprising:
   a container comprising pores in at least a portion of the container;
   a first compartment within the container containing a polymer gel network which undergoes a volume expansion in response to an environmental condition which varies in the biological environment;
   a second compartment containing an effective amount of a biologically active compound in communication with the biological environment through the pores, the first compartment disposed within the second compartment;
   whereupon volume expansion of the polymer gel network causes the biologically active compound to be discharged through the pores of the container into the biological environment through the passageway.

4. Apparatus for controlled delivery of a biologically active compound to a biological environment comprising:
   a container comprised of a single member or two mated and comprising pores in at least a portion of the container, the container defining a space housing:
   upper and lower compartments containing a polymer gel network which undergoes a volume expansion in response to an environmental condition which varies in the biological environment, the upper and lower compartment in communication with the biological environment through the container pores; and
   an inner compartment containing an effective amount of a biologically active compound and including at least one passageway communicating with the biological environment,
   whereupon volume expansion of the polymer gel network causes the biologically active compound to be discharged into the biological environment through the passageway.

5. The apparatus of claim 1, further comprising a biocompatible membrane substantially surrounding the container.

6. The apparatus of claim 1, wherein the environmental condition is pH.

7. The apparatus of claim 1, wherein the polymer gel network is in an expanded state at low pH and in an expanded state had a high pH.

8. The apparatus of claim 1, wherein the apparatus further comprises a partition positioned between the first and second compartments.

9. The apparatus of claim 1, wherein the crosslinked polymer gel network comprises a polymer selected from the group consisting of interpenetrating polymer networks, hydroxypropylcellulose, hydropropylmethylcellulose, starch, and hydroxyethylcellulose.

10. The apparatus of claim 1 wherein the environmental condition is selected from the group consisting of temperature, solvent composition, pH, electric field, magnetic field, light intensity, light wavelength, pressure, ionic strength, osmolarity, electric current, redox potential and presence of specific enzymes.

11. The apparatus of claim 1 wherein the gel network exhibits a continuous volume change.

12. The apparatus of claim 1 wherein the responsive gel network exhibits a discontinuous volume change.

13. The apparatus of claim 1, wherein the container comprises pores over at least a portion of the container defining the second compartment.

14. The apparatus of claim 1, wherein the pores are non-uniformly distributed in the container.

15. The apparatus of claim 1, wherein the pores are of non-uniform diameter.

16. The apparatus of claim 1, wherein the pores are of uniform diameter.

17. The apparatus of claim 8, wherein the partition is fixed within the container and capable of deforming to accommodate the expanding hydrogel.

18. The apparatus of claim 8, wherein the partition is substantially rigid and capable of displacement to accommodate the expanding hydrogel.

19. The apparatus of claim 8, wherein the partition comprises a superabsorbant hydrogel.

20. Apparatus of claim 1, wherein the compartment is implanted into a body.

21. Apparatus of claim 1, wherein the compartment is external to the body.

* * * * *